United States Patent
Tanaka et al.

(10) Patent No.: US 6,770,734 B2
(45) Date of Patent: Aug. 3, 2004

(54) POLYTHIOL COMPOUND

(75) Inventors: Mamoru Tanaka, Fukuoka (JP);
Shigetoshi Kuma, Fukuoka (JP);
Seiichi Kobayashi, Fukuoka (JP);
Yoshinobu Kanemura, Fukuoka (JP)

(73) Assignee: Mitsui Chemicals, Inc., Tokyo (JP)

( * ) Notice: Subject to any disclaimer, the term of this patent is extended or adjusted under 35 U.S.C. 154(b) by 36 days.

(21) Appl. No.: 10/316,180

(22) Filed: Dec. 11, 2002

(65) Prior Publication Data

US 2003/0149230 A1 Aug. 7, 2003

Related U.S. Application Data

(63) Continuation-in-part of application No. 09/817,161, filed on Mar. 27, 2001, now Pat. No. 6,596,841.

(30) Foreign Application Priority Data

Mar. 27, 2000 (JP) ........................................ 2000-086434
Mar. 27, 2000 (JP) ........................................ 2000-086436

(51) Int. Cl.$^7$ .............................................. C08G 75/04
(52) U.S. Cl. ...................................... 528/374; 528/373
(58) Field of Search ................................ 528/374, 373

(56) References Cited

U.S. PATENT DOCUMENTS 6,596,841 B2 * 7/2003 Tanaka et al. ............. 528/374

FOREIGN PATENT DOCUMENTS

EP 1138670 * 10/2001

* cited by examiner

Primary Examiner—Duc Truong
(74) Attorney, Agent, or Firm—Burns, Doane, Swecker & Mathis, L.L.P.

(57) ABSTRACT

A polymerizable composition for a lens with a high refractive index comprising at least one polythiol compound represented general formula (1):

$$R—(SH_2SH)_n \quad (1)$$

where R is an organic residue except an aromatic group and n is an integer of at least 1, having at least two intramolecular mercapto groups and at least one compound having an intramolecular functional group which can react with a mercapto group; a resin prepared by polymerizing the composition; an optical element and a lens made of the resin; and a process for preparing a thiol compound comprising the steps of reacting a compound represented by general formula (2):

$$HS—R^1(—S—R^2)_m \quad (2)$$

where m is an integer of at least 1; $R^1$ represents an aromatic, aliphatic, alicyclic or heterocyclic organic residue or aliphatic, alicyclic or heterocyclic organic residue with an aromatic ring or a sulfur atom in its chain; and $R^2$ represents a protective group, with a compound having a functional group which can react with a mercapto group, and then converting —S—$R^2$ into —SH.

6 Claims, No Drawings

POLYTHIOL COMPOUND

This application is a continuation-in-part application of application Ser. No. 09/817,161 filed Mar. 27, 2001, now U.S. Pat. No. 6,596,841.

BACKGROUND OF THE INVENTION

1. Field of the Invention

This invention relates to a resin used for an optical material such as a plastic lens, a prism, an optical fiber, a substrate for an information recording medium, a filter and a light emitting diode, a polymerizable composition used as a raw material for the resin, and a novel polythiol compound with a higher sulfur content constituting the polymerizable composition. Particularly, these may be suitably used for an eyeglass with a higher refractive index. This invention also relates to a novel process for preparing a thiol with higher sulfur content. A thiol compound prepared by the process, in particular a polythiol compound, may be used as a raw material for preparing an episulfide compound or a resin used for an optical material such as a plastic lens, a prism, an optical fiber, a substrate for an information recording medium, a filter and a light emitting diode. Particularly, it may be suitably used for an eyeglass with a higher refractive index.

2. Description of the Prior Art

A plastic lens is lighter and less brittle than an inorganic lens, and dyeable, which has been therefore rapidly prevailing in the fields of optical devices such as a lens of eyeglasses and a camera lens. Such a plastic lens has been required to exhibit higher performance: e.g., a higher refractive index, a higher Abbe number, a lower specific gravity and improved heat resistance. Various resin materials for a lens have been developed for practical use. Among those, plastic lenses made of a polythiourethane resin proposed by us have been widely used, which have been disclosed in JP-As 60-199016, 62-267316 and 63-46213.

We have further achieved improvement of a refractive index by increasing a sulfur content in a thiol used for a polythiourethane as described in JP-As 2-270859 and 7-252207.

Since further improvement in a refractive index has been, however, required, an episulfide resin has been proposed (JP-As 9-110979, 9-71580, 9-255781 and 10-298287.

According to the processes, a higher refractive index can be achieved while maintaining a relatively higher Abbe number. However, although a polythiourethane resin from a conventional thiol compound may improve a refractive index to some degree, it may have a deficiency of reduced heat resistance which is one of important physical properties, depending on the type of the thiol used. Meanwhile, it has been found that an episulfide resin is less impact-resistant than a polythiourethane resin.

Thus, there has been a need for improved balance among a refractive index, heat resistance and impact resistance in a conventional resin with a higher refractive index.

There have been various attempts to prepare a thiol compound with higher sulfur content for a higher refractive index in a polythiourethane resin. The goal has not been achieved because a useful preparation process has not been established.

That is, it is necessary to develop a method for easily preparing a thiol compound with higher sulfur content.

SUMMARY OF THE INVENTION

An objective of this invention is to provide a polythiol compound which can provide an optical material made of a polythiourethane resin with improved balance among a refractive index, heat resistance and impact resistance.

Another objective of this invention is to provide a resin composition which can provide a polythiourethane resin with improved balance among the above properties.

A further objective of this invention is to provide a polyurethane resin with improved balance among the above properties, which is made of the above resin composition, as well as an optical material made of the resin, particularly a plastic lens.

To solve the problems, we have intensely conducted investigation. Finally, we have developed a novel polythiol compound and a polymerizable composition comprising the compound and have solved all the problems using a resin prepared by the polymerizable composition.

This invention relates to a polythiol compound represented by the general formula (1):

$$R-(SCH_2SH)_n \qquad (1)$$

where R is an organic residue except for an aromatic group and n is an integer of at least 1, having at least two intramolecular mercapto groups and at least one dithioacetal skeleton represented by the following formula:

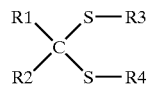

where R1 and R2 are each independently a hydrogen atom or an organic residue except for an aromatic group, which may contain a mercapto group; R3 and R4 are each independently an organic residue except for an aromatic group, which may contain a mercapto group; R1 and R2 are not simultaneously a hydrogen atom; and R1 and R2, R1 and R3 or R4, R2 and R3 or R4, and R3 and R4 may be bonded to form a ring.

According to this invention, a resin with a higher refractive index, higher heat resistance and higher impact resistance with good balance may be provided.

DETAILED DESCRIPTION OF PREFERRED EMBODIMENTS

This invention will be described in detail.

A compound represented by general formula (1) used in this invention is characterized in having a mercaptomethylthio group wherein when n is 1, R representing an organic residue except an aromatic ring has at least one mercapto group and when n is 2 or more, the organic residue R may have a mercapto group or not. Thus, the compound has at least two intramolecular mercapto groups. Herein, R represents an organic residue except an aromatic ring; preferably, a straight or branched aliphatic, alicyclic or heterocyclic organic residue. A straight or branched aliphatic organic residue may have a sulfide or polysulfide bond in its chain. An alicyclic organic residue, in which a mercaptomethylthio group attaches to a ring carbon atom, may have an exocyclic sulfide or polysulfide bond. A heterocyclic organic residue, in which a mercaptomethylthio group attaches to a substitutable atom, may have an endocyclic or exocyclic sulfur-containing sulfide or polysulfide bond.

The polythiol compound represented by formula (1) further has at least one dithioacetal skeleton represented by the following formula:

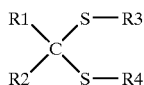

where R1 and R2 are each independently a hydrogen atom or an organic residue except for an aromatic group, which may contain a mercapto group; R3 and R4 are each independently an organic residue except for an aromatic group, which may contain a mercapto group; R1 and R2 are not simultaneously a hydrogen atom; and R1 and R2, R1 and R3 or R4, R2 and R3 or R4, and R3 and R4 may be bonded to form a ring.

The organic residue for R1 to R4 is selected from the group consisting of aliphatic, alicyclic and heterocyclic radicals as well as aliphatic, alicyclic and heterocyclic radicals containing a sulfur atom in their chain.

Examples of a polythiol compound represented by general formula (1) include, but are not limited to, 3,3-dimercaptomethyl-1,5-dimercapto-2,4-dithiapentane, 3-mercaptomethyl-1,5-dimercapto-2,4-dithiapenane, 3-mercaptomethylthio-1,5-dimercapto-2-thiapentane, 1,1,2,2-tetrakis(mercapto-methylthio)ethane, 1,1,3,3,-tetrakis (mercaptomethylthio)propane, 4,5-bis (mercaptomethylthio)-1,3-dithiolane, 4,6-bis (mercaptomethylthio)-1,3-dithiane, 2-bis (mercaptomethylthio)methyl-1,3-dithiethane, 2-(2,2-bis (mercaptomethylthio)ethyl)-1,3-dithiethane.

These polythiol compounds may be used alone or in combination of two or more.

A polythiol compound other than a polythiol compound represented by general formula (1) may be, if necessary, combined.

Examples of a compound which may be combined include aliphatic polythiol compounds such as methanedithiol, ethanedithiol, 1,1-propanedithiol, 1,2-propanedithiol, 1,3-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, 1,1-bis(mercaptomethyl)cyclohexane, bis(2-mercaptoethyl)thiomalate, 2,3-dimercapto-1-propanol (2-mercaptoacetate), 2,3-dimercapto-1-propanol (3-mercaptopropionate), diethyleneglycol bis(2-mercaptoacetate), diethyleneglycol bis(3-mercaptopropionate), 1,2-dimercaptopropyl methyl ether, 2,3-dimercaptopropyl methyl ether, 2,2-bis (mercaptomethyl)-1,3-propanedithiol, bis(2-mercaptoethyl) ether, ethyleneglycol bis(2-mercaptoacetate), ethyleneglycol bis(3-mercaptopropionate), trimethylolpropane bis(2-mercaptoacetate), trimethylolpropane bis(3-mercaptopropionate), pentaerythritol tetrakis(2-mercaptoacetate), pentaerythritol tetrakis(3-mercaptopropionate) and tetrakis(mercaptomethyl)methane;

aromatic polythiol compounds such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis (mercaptomethyl)benzene, 1,2-bis(mercaptoethyl) benzene, 1,3-bis(mercaptoethyl)benzene, 1,4-bis (mercaptomethyl)benzene, 1,2,3-trimercaptobenzene, 1,2,4-trimercaptobenzene, 1,3,5-trimercaptobenzene, 1,2,3-tris(mercaptomethyl)benzene, 1,2,4-tris (mercaptomethyl)benzene, 1,3,5-tris(mercaptomethyl) benzene, 1,2,3-tris(mercaptoethyl)benzene, 1,2,4-tris (mercaptoethyl)benzene, 1,3,5-tris(mercaptoethyl) benzene, 2,5-toluenedithiol, 3,4-toluenedithiol, 1,3-di (p-methoxyphenyl)propane-2,2-dithiol, 1,3-diphenylpropane-2,2-dithiol, phenylmethane-1,1-dithiol and 2,4-di(p-mercaptophenyl)pentane;

aromatic polythiol compounds containing a sulfur atom in addition to a mercapto group such as 1,2-bis (mercaptoethylthio)benzene, 1,3-bis (mercaptoethylthio)benzene, 1,4-bis (mercaptoethylthio)benzene, 1,2,3-tris (mercaptomethylthio)benzene, 1,2,4-tris (mercaptomethylthio)benzene, 1,3,5-tris (mercaptomethylthio)benzene, 1,2,3-tris (mercaptoethylthio)benzene, 1,2,4-tris (mercaptoethylthio)benzene and 1,3,5-tris (mercaptoethylthio)benzene as well as their nuclear alkylated derivatives;

sulfides such as bis(mercaptomethyl) sulfide, bis (mercaptoethyl) sulfide, bis(mercaptopropyl) sulfide, bis(2-mercaptoethylthio)methane, bis(3-mercaptopropylthio)methane, 1,2-bis(2-mercaptoethylthio)ethane, 1,2-bis(3-mercaptopropylthio)ethane, 1,3-bis(2-mercaptoethylthio)propane, 1,3-bis(3-mercaptopropylthio)propane, 1,2,3-tris(2-mercaptoethylthio)propane, 1,2,3-tris(3-mercaptopropylthio)propane, 1,2-bis[(2-mercaptoethyl)thio]-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl 1,11-dimercapto-3,6,9-trithiaundecane, tetrakis(2-mercaptoethylthiomethyl) methane, tetrakis(3-mercaptopropylthiomethyl) methane, bis(2,3-dimercaptopropyl) sulfide, bis(1,3-dimercaptopropyl) sulfide, 2,5-dimercapto-1,4-dithiane, 2,5-dimercaptomethyl-1,4-dithiane, 2,5-dimercaptomethyl-2,5-dimethyl-1,4-dithiane, bis (mercaptoethyl) disulfide and bis(mercaptopropyl) disulfide as well as their thioglycolates and mercaptopropionates;

aliphatic polythiol compounds containing a sulfur atom in addition to a mercapto group such as hydroxymethylsulfide bis(2-mercaptoacetate), hydroxymethylsulfide bis(3-mercaptopropionate), hydroxyethylsulfide bis(2-mercaptoacetate), hydroxyethylsulfide bis(3-hydroxypropylsulfide bis(2-mercaptoacetate), hydroxypropylsulfide bis(3-mercaptopropionate), hydroxymethyldisulfide bis(2-mercaptoacetate), hydroxymethyldisulfide bis(3-mercaptopropionate), hydroxyethyldisulfide bis(2-mercaptoacetate), hydroxyethyldisulfide bis(3-mercaptopropionate), hydroxypropyldisulfide bis(2-mercaptoacetate), hydroxypropyldisulfide bis(3-mercaptopropionate), 2-mercaptoethylether bis(2-mercaptoacetate), 2-mercaptoethylether bis(3-mercaptopropionate), 1,4-dithiane-2,5-diol bis(2-mercaptoacetate), 1,4-dithiane-2,5-diol bis(3-mercaptopropionate), bis(2-mercaptoethyl) thiodiglycolate, bis(2-mercaptoethyl) thiodipropionate, bis(2-mercaptoethyl) 4,4-thiodibutyrate, bis(2-mercaptoethyl) dithiodiglycolate, bis(2-mercaptoethyl) dithiodipropionate, bis(2-mercaptoethyl) 4,4-dithiodibutyrate, bis(2,3-dimercaptopropyl) thiodiglycolate, bis(2,3-dimercaptopropyl) thiodipropionate, bis(2,3-dimercaptopropyl) dithiodiglycolate and bis(2,3-dimercaptopropyl) dithiodipropionate;

heterocyclic compounds containing a sulfur atom in addition to a mercapto group such as 3,4-thiophenedithiol and 2,5-dimercapto-1,3,4-thiadiazole; and compounds containing a hydroxy group in addition to a mercapto group such as 2-mercaptoethanol, 3-mercapto-1,2-propanediol, glyceryl di(mercaptoacetate), 1-hydroxy-4-mercaptocyclohexane, 2,4-dimercaptophenol, 2-mercaptohydroquinone, 4-mercaptophenol, 3,4-dimercapto-2-propanol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopriopionate), pentaerythritol bis (3-mercaptopropionate), pentaerythritol tris(thioglycolate), dipentaerythritol pentakis(3-mercaptopropionate), hydroxymethyl-tris (mercaptoethylthiomethyl)methane and 1-hydroxyethylthio-3-mercaptoethylthiobenzene. These compounds may be halogenated (e.g., chlorinated or brominated).

Examples of a compound having a functional group which can react with a mercapto group used in this invention include iso(thio)cyanates, (thio)epoxy compounds and compounds having an intramolecular unsaturated group which can react with a mercapto group.

Specifically, an iso(thio)cyanate has at least one intramolecular iso(thio)cyanate group, including aliphatic polyisocyanates such as hexamethylene diisocyanate, 2,2-dimethylpentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, bis(isocyanatoethyl) carbonate, bis(isocyanatoethyl) ether, lysine diisocyanatomethyl ester, lysine triisocyanate, xylylene diisocyanate, bis(isocyanatoethyl)benzene, bis(isocyanatopropyl)benzene, α, α, α', α'-tetramethylxylylene diisocyanate, bis(isocyanatobutyl)benzene, bis(isocyanatomethyl)naphthalene, bis(isocyanatomethylphenyl)ether, bis(isocyanatoethyl) phthalate and 2,6-di(isocyanatomethyl)furane;

alicyclic polyisocyanates such as isophorone diisocyanate, bis(isocyanatomethyl)cyclohexane, cyclohexane diisocyanate, methylcyclohexane diisocyanate, 4,4'-methylenebis(cyclohexylisocyanate), 4,4'-methylenebis(2-methylcyclohexylisocyanate), 2,5-bis(isocyanatomethyl)bicyclo-[2.2.1]-heptane, 2,6-bis(isocyanatomethyl)bicyclo-[2.2.1]-heptane, 3,8-bis(isocyanatomethyl)tricyclodecane, 3,9-bis(isocyanatomethyl)tricyclodecane, 4,8-bis(isocyanatomethyl)tricyclodecane and 4,9-bis(isocyanatomethyl)tricyclodecane;

aromatic polyisocyanates such as 1,2-diisocyanatobenzene, 1,3-diisocyanatobenzene, 1,4-diisocyanatobenzene, 2,4-diisocyanatotoluene, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluidine diisocyanate, 4,4'-methylene bis(phenylisocyanate), 4,4'-methylene bis(2-methylphenylisocyanate), bibenzyl-4,4'-diisocyanate and bis(isocyanatophenyl) ethylene;

sulfur-containing aliphatic polyisocyanates such as bis (isocyanatomethyl) sulfide, bis(isocyanatoethyl) sulfide, bis(isocyanatopropyl) sulfide, bis(isocyanatohexyl) sulfide, bis(isocyanatomethyl) sulfone, bis(isocyanatomethyl) disulfide, bis(isocyanatoethyl) disulfide, bis(isocyanatopropyl) disulfide, bis(isocyanatomethylthio)methane, bis(isocyanatoethylthio)methane, bis(isocyanatoethylthio) ethane, bis(isocyanatomethylthio)ethane, 1,5-diisocyanato-2-isocyanatomethyl-3-thiapentane, 1,2,3-tris(isocyanatomethylthio)propane, 1,2,3-tris(isocyanatoethylthio)propane, 3,5-dithia-1,2,6,7-heptane tetraisocyanate, 2,6-diisocyanatomethyl-3,5-dithia-1,7-heptane diisocyanate, 2,5-diisocyanatomethylthiophene and 4-isocyanatoethylthio-2,6-dithia-1,8-octane-diisocyanate;

aromatic sulfide polyisocyanates such as 2-isocyanatophenyl 4-isocyanatophenyl sulfide, bis(4-isocyanatophenyl) sulfide and bis(4-isocyanatomethylphenyl) sulfide;

aromatic disulfide polyisocyanates such as bis(4-isocyanatophenyl) disulfide, bis(2-methyl-5-isocyanatophenyl) disulfide, bis(3-methyl-5-isocyanatophenyl) disulfide, bis(3-methyl-6-isocyanatophenyl) disulfide, bis(4-methyl-5-isocyanatophenyl) disulfide, bis(3-methoxy-4-isocyanatophenyl) disulfide and bis(4-methoxy-3-isocyanatophenyl) disulfide;

sulfur-containing alicyclic polyisocyanates such as 2,5-diisocyanatotetrahydrothiophene, 2,5-diisocyanatomethyltetrahydrothiophene, 3,4-diisocyanatomethyltetrahydrothiophene, 2,5-diisocyanato-1,4-dithiane, 2,5-diisocyanatomethyl-1,4-dithiane, 4,5-diisocyanato-1,3-dithiolane, 4,5-bis(isocyanatomethyl)-1,3-dithiolane and 4,5-diisocyanatomethyl-2-methyl-1,3-dithiolane;

aliphatic polyisothiocyanates such as 1,2-diisothiocyanatoethane and 1,6-diisothiocyanatohexane;

alicyclic polyisothiocyanates such as cyclohexanediisothiocyanate;

aromatic polyisothiocyanates such as 1,2-diisothiocyanatobenzene, 1,3-diisothiocyanatobenzene, 1,4-diisothiocyanatobenzene, 2,4-diisothiocyanatotoluene, 2,5-diisothiocyanato-m-xylene, 4,4'-diisothiocyanatobiphenyl, 4,4'-methylene bis(phenylisothiocyanate), 4,4'-methylene bis(2-methylphenylisothiocyanate), 4,4'-methylene bis(3-methylphenylisothiocyanate), 4,4'-isopropylidene bis(phenylisothiocyanate), 4,4'-diisothiocyanatobenzophenone, 4,4'-diisothiocyanato-3,3'-dimethylbenzophenone and bis(4-isothiocyanatophenyl) ether;

carbonylpolyisothiocyanates such as 1,3-benzenedicarbonyl diisothiocyanate, 1,4-benzenedicarbonyl diisothiocyanate and (2,2-pyridine)-4,4-dicarbonyl diisothiocyanate;

sulfur-containing aliphatic polyisothiocyanates such as thiobis(3-isothiocyanatopropane), thiobis(2-isothiocyanatoethane) and dithiobis(2-isothiocyanatoethane);

sulfur-containing aromatic polyisothiocyanates such as 1-isothiocyanato-4-[(2-isothiocyanato)sulfonyl] benzene, thiobis(4-isothiocyanatobenzene), sulfonylbis (4-isothiocyanatobenzene) and dithiobis(4-isothiocyanatobenzene);

sulfur-containing alicyclic polyisothiocyanates such as 2,5-diisothiocyanatothiophene and 2,5-diisothiocyanato-1,4-dithiane; and compounds having an isocyanate and an isothiocyanate groups such as 1-isocyanato-6-isothiocyanatohexane, 1-isocyanato-4-isothiocyanatocyclohexane, 1-isocyanato-4-isothiocyanatobenzene, 4-methyl-3-isocyanato-1-isothiocyanatobenzene, 2-isocyanato-4,6-diisothiocyanato-1,3,5-triazine, 4-isocyanatophenyl-4-isothiocyanatophenyl sulfide and 2-isocyanatoethyl-2-isothiocyanatoethyl disulfide.

In this invention may be used the above compounds which are halogenated (e.g., chlorinated or brominated), alkylated, alkoxylated, nitrated, modified with a polyol into a prepolymer, carbodiimide-modified, urea-modified, biuret-modified, dimerized or trimerized.

Examples of a (thio)epoxy compound which has at least one intramolecular (thio)epoxy group include acyclic aliphatic 2,3-epithiopropylthio compounds such as bis(2,3-epithiopropyl)disulfide, bis(2,3-epithiopropyl)sulfide, bis(2,3-epithiopropylthio)methane, 1,2-bis(2,3-epithiopropylthio)ethane, 1,2-bis(2,3-epithiopropylthio)propane, 1,3-bis(2,3-epithiopropylthio)propane, 1,3-bis(2,3-epithiopropylthio)-2-methylpropane, 1,4-bis(2,3-epithiopropylthio)butane, 1,4-bis(2,3-epithiopropylthio)-2-methylbutane, 1,3-bis(2,3-epithiopropylthio)butane, 1,5-bis(2,3-epithiopropylthio)pentane, 1,5-bis(2,3-epithiopropylthio)-2-methylpentane, 1,5-bis(2,3-epithiopropylthio)-3-thiapentane, 1,6-bis(2,3-epithiopropylthio)hexane, 1,6-bis(2,3-epithiopropylthio)-2-methylhexane, 3,8-bis(2,3-epithiopropylthio)-3,6-dithiaoctane, 1,2,3-tris(2,3-epithiopropylthio)propane, 2,2-bis(2,3-epithiopropylthiomethyl)-1,3-bis(2,3epithiopropylthio)propane, 2,2-bis(2,3-epithiopropylthiomethyl)-1-(2,3-epithiopropylthio)butane, 1,5-bis(2,3-epithiopropylthio)-2-(2,3-epithiopropylthiomethyl)-3-thiapentane, 1,5-bis(2,3-epithiopropylthio)-2,4-bis(2,3-epithiopropylthiomethyl)-3-thiapentane, 1-(2,3-epithiopropylthio)-2,2-bis(2,3-epithiopropylthiomethyl)-4-thiahexane, 1,5,6-tris(2,3-epithiopropylthio)-4-(2,3-epithiopropylthiomethyl)-3-thiahexane, 1,8-bis(2,3-epithiopropylthio)-4-(2,3-epithiopropylthiomethyl)-3,6-dithiaoctane, 1,8-bis(2,3-epithiopropylthio)-4,5-bis(2,3-epithiopropylthiomethyl)-3,6-dithiaoctane, 1,8-bis(2,3-epithiopropylthio)-4,4-bis(2,3-epithiopropylthiomethyl)-3,6-dithiaoctane, 1,8-bis(2,3-epithiopropylthio)-2,5-bis(2,3-epithiopropylthiomethyl)-3,6-dithiaoctane, 1,8-bis(2,3-epithiopropylthio)-2,4,5-tris(2,3-epithiopropylthiomethyl)-3,6-dithiaoctane, 1,1,1-tris{[2-(2,3-epithiopropylthio)ethyl]thiomethyl}-2-(2,3-epithiopropylthio)ethane, 1,1,2,2-tetrakis{[2-(2,3-epithiopropylthio)ethyl]thiomethyl}ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis(2,3-epithiopropylthiomethyl)-3,6,9-trithiaundecane and 1,11-bis(2,3-epithiopropylthio)-5,7-bis(2,3-epithiopropylthiomethyl)-3,6,9-trithiaundecane;

alicyclic 2,3-epithiopropylthio compounds such as 1,3-bis(2,3-epithiopropylthio)cyclohexane, 1,4-bis(2,3-epithiopropylthio)cyclohexane, 1,3-bis(2,3-epithiopropylthiomethyl)cyclohexane, 1,4-bis(2,3-epithiopropylthiomethyl)cyclohexane, 2,5-bis(2,3-epithiopropylthiomethyl)-1,4-dithiane, 2,5-bis{[2-(2,3-epithiopropylthio)ethyl]thiomethyl}-1,4-dithiane and 2,5-bis(2,3-epithiopropylthiomethyl)-2,5-dimethyl-1,4dithiane;

aromatic 2,3-epithiopropylthio compounds such as 1,2-bis(2,3-epithiopropylthio)benzene, 1,3-bis(2,3-epithiopropylthio)benzene, 1,4-bis(2,3-epithiopropylthiol)benzene, -epithiopropylthiomethyl)benzene, 1,2-bis(2,3-epithiopropylthio)benzene, 1,3-bis(2,3-epithiopropylthiomethyl)benzene, 1,4-bis(2,3-epithiopropylthiomethyl)benzene, bis[4-(2,3-epithiopropylthio)phenyl]methane, 2,2-bis[4-(2,3-epithiopropylthio)phenyl]propane, bis[4-(2,3-epithiopropylthio)phenyl]sulfide, bis[4-(2,3-epithiopropylthio-phenyl]sulfone and 4,4'-bis(2,3-epithiopropylthio)-biphenyl; and mercapto-containing epithio compounds such as 3-mercaptopropylene sulfide and 4-mercaptobutene sulfide.

Examples of a compound having at least one unsaturated bond which can react with a mercapto group include, but not limited to, (meth)acrylates such as benzyl (meth)acrylate, butoxyethyl (meth)acrylate, butoxymethyl (meth)acrylate, cyclohexyl (meth)acrylate, 2-hydroxyethyl (meth)acrylate, glycidyl (meth)acrylate, thioglycidyl (meth)acrylate, phenoxyethyl (meth)acrylate, phenyl (meth)acrylate, ethyleneglycol di(meth)acrylate, diethyleneglycol di(meth)acrylate, triethyleneglycol di(meth)acrylate, tetraethyleneglycol di(meth)acrylate, polyethyleneglycol di(meth)acrylate, neopentylglycol di(meth)acrylate, bisphenol-A di(meth)acrylate, 2,2-bis(4-(meth)acryloyloxyethoxyphenyl)propane, 2,2-bis(4-(meth)acryloyoxylethoxyethoxyphenyl)propane, bisphenol-F di(meth)acrylate, bis(4-(meth)acryloyloxyethoxyphenyl)methane, 1,1-bis(4-(meth)acryloxyethoxyethoxyphenyl)methane, trimethylolpropane tri(meth)acrylate, glycelol di(meth)acrylate, pentaerythritol tri(meth)acrylate and pentaerythritol tetra(meth)acrylate;

thio(meth)acrylates such as (meth)acryloylthioethane, (meth)acryloylthiomethylbenzene, 1,2-bis[(meth)acryloylthio]ethane, 1,3-bis[(meth)acryloylthio]propane, 1,4-bis[(meth)acryloylthio]butane, 1,6-bis[(meth)acryloylthio]hexane, bis[2-(meth)acryloylthioethyl]ether, bis[2-(meth)acryloylthioethyl]sulfide, bis[2-(meth)acryloylthioethylthio]methane, 1,2-bis[2-(meth)acryloylthioethylthio]-3-(meth)acryloylthiopropane, thioglycidyl thio(meth)acrylate, glycidyl thio(meth)acrylate, 1,2-bis[(meth)acryloylthio]benzene, 1,3-bis[(meth)acryloylthio]benzene, 1,4-bis[(meth)acryloylthio]benzene, 1,2-bis[(meth)acryloylthiomethyl]benzene, 1,3-bis[(meth)acryloylthiomethyl]benzene, 1,4-bis[(meth)acryloylthiomethyl]benzene, 1,2-bis[2-(meth)acryloylthioethylthiomethyl]benzene, 1,3-bis[2-(meth)acryloylthioethylthiomethyl]benzene and 1,4-bis[2-(meth)acryloylthioethylthiomethyl]benzene;

allyl compounds such as allyl glycidyl ether, diallyl phthalate, diallyl terephthalate, diallyl isophthalate, diallyl carbonate, diethyleneglycol bisallyl carbonate, diallyl sulfide and diallyl disulfide;

vinyl compounds such as styrene, chlorostyrene, methylstyrene, bromostyrene, dibromostyrene, divinylbenzene and 3,9-divinylspirobi(m-dioxane); and diisopropenylbenzene.

These compounds having a functional group which can react with a mercapto group may be, regardless of the type of the functional group, used alone or in combination of two or more.

A polymerizable composition of this invention may contain a resin modifier for mainly improving monomer or resin properties, e.g., adjusting optical properties such as a refractive index; and physical properties such as impact resistance and a specific gravity, as well as handling properties such as the viscosity of the polymerizable composition.

For molding a polymerizable composition of this invention, a variety of substances such as chain extenders, crosslinking agents, photostabilizers, UV absorbers, antioxidants, anti-coloring agents, blueing agents, oil soluble dyes and fillers may be added, depending on a purpose, as in the known molding methods.

For adjusting a reaction rate, a known reaction catalyst may be added as appropriate. Examples of a preferably used catalyst include, for example as a urethanation catalyst, tin compounds such as dibutyltin dilaurate, dibutyltin dichloride and dimethyltin dichloride and amine compounds such as tertiary amines, which may be used alone or in combination. Catalysts which may be used include amines, phosphines, Lewis acids, radical polymerization catalysts and cation polymerization catalysts for a mixture of (thio) epoxy compounds and radical polymerization catalysts and photosensitizers for a mixture of polyene compounds.

A resin prepared by polymerization of a polymerizable composition of this invention may be usually prepared by cast polymerization. Specifically, monomers used are mixed with various additives such as a catalyst, an ultraviolet absorber and an internal mold release agent in advance to prepare a mixed solution. Here, variety of additives may be added to a part of monomers and then the remaining monomers and additives may be added. The mixed solution is degassed by an appropriate method if necessary and then polymerized by heating or irradiation. In particular, the composition may be poured into a mold consisting of two glass plates and a tape or gaskets and then polymerized for lens preparation.

Polymerization conditions cannot be generalized since they considerably vary depending on various factors such as the type of monomers used, the type and the amount of a catalyst and the shape of a mold, but heat polymerization may be conducted at a temperature of about −20° C. to 200° C. for 1 to 100 hours. Meanwhile, photopolymerization may be conducted using light from a source such as a high-pressure mercury-vapor lamp, a halogen lamp, a xenon lamp, a tungsten lamp, a fluorescent lamp or sunlight. A removed lens may be, if necessary, subjected to treatment such as annealing.

A resin of this invention thus obtained is colorless and transparent, exhibits good optical and mechanical properties and is suitable as an optical device material such as eyeglass lenses and a camera lens.

Furthermore, a lens made of the optical resin of this invention may be, if necessary, subjected to physical or chemical treatments such as surface abrasion, antistatic treatment, hard coating, non-reflection coating and dyeing, for improvements such as prevention of reflection; improvement in hardness, abrasion resistance or chemical resistance; and impartation of antifoggy or cosmetic property.

This invention also relates to a process for preparing a thiol compound comprising the steps of reacting a compound represented by general formula (2):

$$HS-R^1(-S-R^2)_m \qquad (2)$$

where m is an integer of at least 1; $R^1$ represents an aromatic, aliphatic, alicyclic or heterocyclic organic residue or aliphatic, alicyclic or heterocyclic organic residue with an aromatic ring or a sulfur atom in its chain; and $R^2$ represents a protective group, with a compound having a functional group which can react with a mercapto group, and then converting —S—$R^2$ into —SH.

In general formula (2), an organic residue $R^1$ may be a straight or branched aliphatic organic residue, an alicyclic organic residue, an aromatic organic residue, a heterocyclic residue; a straight or branched aliphatic organic residue having a sulfur atom in a form of sulfide or polysulfide bonding or an aromatic ring in its chain; or an alicyclic organic residue having a sulfur atom in a form of sulfide or polysulfide bonding or an aromatic ring.

In general formula (2), examples of a protective group $R^2$ include, but not limited to, carbonyls such as acetyl, propionoyl, butyroyl, isobutyroyl, valeroyl, isovaleroyl, hexanoyl, heptanoyl, benzoyl and phenylacetyl; carbamoyls such as ethylcarbamoyl, propylcarbamoyl, butylcarbamoyl, hexylcarbamoyl, phenylcarbamoyl and benzylcarbamoyl and sulfides such as methylthio, ethylthio, hydroxyethylthio, propylthio, butylthio, phenylthio and benzylthio.

A compound represented by general formula (2) used in this invention is a common polythiol compound in which at least one mercapto group remains while the other mercapto groups are protected with the above protective group.

Examples of a common polythiol described above include aliphatic polythiols such as methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, 1,1-bis(mercaptomethyl)cyclohexane, bis(2-mercaptoethyl)thiomalate, 2,3-dimercapto-1-propanol (2-mercaptoacetate), 2,3-dimercapto-1-propanol (3-mercaptopropionate), diethyleneglycol bis(2-mercaptoacetate), diethyleneglycol bis(3-mercaptopropionate), 1,2-dimercaptopropyl methyl ether, 2,3-dimercaptopropyl methyl ether, 2,2-bis (mercaptomethyl)-1,3-propanedithiol, bis(2-mercaptoethyl) ether, ethyleneglycol bis(2-mercaptoacetate), ethyleneglycol bis(3-mercaptopropionate), trimethylolpropane bis(2-mercaptoacetate), trimethylolpropane bis(3-mercaptopropionate), pentaerythritol tetrakis(2-mercaptoacetate), pentaerythritol tetrakis(3-mercaptopropionate) and tetrakis(mercaptomethyl)methane;

aromatic polythiols such as 1,2-benzenedithiol, 1,3-benzenedithiol, 1,4-benzenedithiol, 1,2-bis (mercaptomethyl)benzene, 1,3-bis(mercaptomethyl) benzene, 1,4-bis(mercaptomethyl)benzene, 1,2-bis (mercaptoethyl)benzene, 1,3-bis(mercaptoethyl) benzene, 1,4-bis(mercaptoethyl)benzene, 1,2,3-trimercaptobenzene, 1,2,4-trimercaptobenzene, 1,3,5-trimercaptobenzene, 1,2,3-tris(mercaptomethyl) benzene, 1,2,4-tris(mercaptomethyl)benzene, 1,3,5-tris (mercaptomethyl)benzene, 1,2,3-tris(mercaptoethyl) benzene, 1,2,4-tris(mercaptoethyl)benzene, 1,3,5-tris (mercaptoethyl)benzene, 2,5-toluenedithiol, 3,4-toluenedithiol, 1,3-di(p-methoxyphenyl)propane-2,2-dithiol, 1,3-diphenylpropane-2,2-dithiol, phenylmethane-1,1-dithiol and 2,4-di(p-mercaptophenyl)pentane;

aromatic polythiols containing a sulfur atom in addition to a mercapto group such as 1,2-bis(mercaptoethylthio) benzene, 1,3-bis(mercaptoethylthio)benzene, 1,4-bis (mercaptoethylthio)benzene, 1,2,3-tris (mercaptomethylthio)benzene, 1,2,4-tris (mercaptomethylthio)benzene, 1,3,5-tris (mercaptomethylthio)benzene, 1,2,3-tris (mercaptoethylthio)benzene, 1,2,4-tris (mercaptoethylthio)benzene and 1,3,5-tris (mercaptoethylthio)benzene as well as their nuclear alkylated derivatives;

sulfides such as bis(mercaptomethyl) sulfide, bis (mercaptoethyl) sulfide, bis(mercaptopropyl) sulfide, bis(mercaptomethylthio)methane, bis(2-mercaptoethylthio)methane, bis(3-mercaptopropylthio) methane, 1,2-bis(2-mercaptoethylthio)ethane, 1,2-bis (3-mercaptopropyl)ethane, 1,3-bis(3-mercaptopropylthio)propane, 1,2,3-tris(2-mercaptoethylthio)propane, 1,2,3-tris(3-mercaptopropylthio)propane, 1,2-bis[(2-mercaptoethyl)thio]-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, tetrakis(2-mercaptoethylthiomethyl)methane, tetrakis(3-mercaptopropylthiomethyl)methane, bis(2,3-dimercaptopropyl)sulfide, bis(1,3-dimercaptopropyl) sulfide, 2,5-dimercapto-1,4-dithiane, 2,5-dimercaptomethyl-1,4-dithiane, 2,5-dimercaptomethyl-2,5-dimethyl-1,4-dithiane, bis(mercaptoethyl) disulfide and bis(mercaptopropyl) disulfide as well as their thioglycolates and mercaptopropionates;

aliphatic polythiol compounds containing a sulfur group in addition to a mercapto group such as hydroxymethylsulfide bis(2-mercaptoacetate), hydroxymethylsulfide bis(3-mercaptopropionate), hydroxyethylsulfide bis(2-mercaptoacetate), hydroxyethylsulfide bis(3-mercaptopropionate), hydroxypropylsulfide bis(2-mercaptoacetate), hydroxypropylsulfide bis(3-mercaptopropionate), hydroxymethyldisulfide bis(2-mercaptoacetate), hydroxymethyldisulfide bis(3-mercaptopropionate), hydroxyethyldisulfide bis(2-mercaptoacetate), hydroxyethyldisulfide bis(3-mercaptopropionate), hydroxypropyldisulfide bis(2-mercaptoacetate), hydroxypropyldisulfide bis(3-mercaptopropionate), 2-mercaptoethylether bis(2-mercaptoacetate), 2-mercaptoethylether bis(3-mercaptopropionate), 1,4-dithiane-2,5-diol bis(2-mercaptoacetate), 1,4-dithiane-2,5-diol bis(3-mercaptopropionate), bis(2-mercaptoethyl) thiodiglycolate, bis(2-mercaptoethyl) thiodipropionate, bis(2-mercaptoethyl) 4,4-thiodibutyrate, bis(2-mercapto ethyl) dithiodiglycolate, bis(2-mercaptoethyl) dithiodipropionate, bis(2-mercaptoethyl) 4,4-dithiodibutyrate, bis(2,3-dimercaptopropyl) thiodiglycolate, bis(2,3-dimercaptopropyl) thiodipropionate, bis(2,3-dimercaptopropyl) dithiodiglycolate and bis(2,3-dimercaptopropyl) dithiodipropionate;

heterocyclic compounds containing a sulfur group in addition to a mercapto group such as 3,4-thiophenedithiol and 2,5-dimercapto-1,3,4-thiadiazole; and compounds containing a hydroxy group in addition to a mercapto group such as 2-mercaptoethanol, 3-mercapto-1,2-propanediol, glyceric di(mercaptoacetate), 1-hydroxy-4-mercaptocyclohexane, 2,4-dimercaptophenol, 2-mercaptohydroquinone, 4-mercaptophenol, 3,4-dimercapto-2-propanol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), pentaerythritol bis(3-mercaptopropionate), pentaerythritol tris(thioglycolate), dipentaerythritol pentakis(3-mercaptopropionate), hydroxymethyl tris(mercaptoethylthiomethyl)methane and 1-hydroxyethylthio-3-mercaptoethylthiobenzene. In these compounds which may be halogenated (e.g., chlorinated or brominated), one mercapto group may remain while the other mercapto groups may be protected with a protective group.

Preferable compounds are exemplified methanedithiol, ethanedithiol, bis(mercaptomethyl) sulfide and bis (mercaptoethyl) sulfide, more preferably methanedithiol in which one mercapto group is protected with a protective group.

Examples of a compound having a functional group which can react with a mercapto group used in this invention include aldehydes, acetals, ketones, (thio)epoxy compounds, compounds having an unsaturated bond which can react with a mercapto group, iso(thio)cyanates and thiols.

Examples of aldehydes, acetals and ketones include aldehydes such as formaldehyde, acetoaldehyde, propionaldehyde, butylaldehyde, benzaldehyde, glyoxal, malonaldehyde, 2-thiophenealdehyde, methylbenzaldehyde and phthalaldehyde as well as their acetals; and ketones such as acetone, acetophenone, benzophenone, methyl ethyl ketone, cyclopentanone and cyclohexanedione. Such a compound may react with an unprotected mercapto group in a compound represented by general formula (2) in the presence of an acid catalyst such as p-toluenesulfonic acid and methanesulfonic acid to give a dithioacetal compound after dehydration or dealcoholization.

Examples of a (thio)epoxy compound include acyclic aliphatic 2,3-epithiopropylthio compounds such as bis(2,3-epithiopropyl) disulfide bis(2,3-epithiopropyl) sulfide, bis(2,3-epithiopropylthio)methane, 1,2-bis(2,3-epithiopropylthio)ethane, 1,2-bis(2,3-epithiopropylthio)propane, 1,3-bis(2,3-epithiopropylthio)propane, 1,3-bis(2,3-epithiopropylthio)-2-methylpropane, 1,4-bis(2,3-epithiopropylthio)butane, 1,4-bis(2,3-epithiopropylthio)-2-methylbutane, 1,3-bis(2,3-epithiopropylthio)butane, 1,5-bis(2,3-epithiopropylthio)pentane, 1,5-bis(2,3-epithiopropylthio)-2-methylpentane, 1,5-bis(2,3-epithiopropylthio)-3-thiapentane, 1,6-bis(2,3-epithiopropylthio)hexane, 1,6-bis(2,3-epithiopropylthio)-2-methylhexane, 3,8-bis(2,3-epithiopropylthio)-3,6-dithiaoctane, 1,2,3-tris(2,3-epithiopropylthio)propane, 2,2-bis(2,3-epithiopropylthiomethyl)-1,3-bis (2,3-epithiopropylthio)propane, 2,2-bis(2,3-epithiopropylthiomethyl)-1-(2,3-epithiopropylthio)butane, 1,5-bis(2,3-epithiopropylthio)-2-(2,3-epithiopropylthiomethyl)-3-thiapentane, 1,5-bis(2,3-epithiopropylthio)-2,4-bis(2,3-epithiopropylthiomethyl)-3-thiapentane, 1-(2,3-epithiopropylthio)-2,2-bis (2,3-epithiopropylthiomethyl)-4-thiahexane, 1,5,6-tris(2,3-epithiopropylthio)-4-(2,3-epithiopropylthiomethyl)-3-thiahexane, 1,8-bis(2,3-epithiopropylthio)-4-(2,3-epithiopropylthiomethyl)-3,6-dithiaoctane, 1,8-bis(2,3-epithiopropylthio)-4,5-bis(2,3-epithiopropylthiomethyl)-3,6-dithiaoctane, 1,8-bis(2,3-epithiopropylthio)-4,4-bis(2,3-epithiopropylthiomethyl)-3,6-dithiaoctane, 1,8-bis(2,3-epithiopropylthio)-2,5-bis(2,3-epithiopropylthiomethyl)-3,6-dithiaoctane, 1,8-bis(2,3-epithiopropylthio)-2,4,5-tris(2,3-epithiopropylthiomethyl)-3,6-dithiaoctane, 1,1,1-tris{[2-(2,3-epithiopropylthio)ethyl]thiomethyl}-2-(2,3-epithiopropylthio)ethane, 1,1,2,2-tetrakis{[2-(2,3-epithiopropylthio)ethyl]thiomethyl}ethane, 1,11-bis(2,3-epithiopropylthio)-4,8-bis(2,3-epithiopropylthiomethyl)-3,6,9-trithiaundecane, 1,11-bis(2,3-epithiopropylthio)-4,7-bis(2,3-epithiopropylthiomethyl)-3,6,9-trithiaundecane and 1,11-bis(2,3-epithiopropylthio)-5,7-bis(2,3-epithiopropylthiomethyl)-3,6,9-trithiaundecane;

alicyclic 2,3-epithiopropylthio compounds such as 1,3-bis(2,3-epithiopropylthio)cyclohexane, 1,4-bis(2,3-epithiopropylthio)cyclohexane, 1,3-bis(2,3-epithiopropylthiomethyl)cyclohexane, 1,4-bis(2,3-epithiopropylthiomethyl)cyclohexane, 2,5-bis(2,3- epithiopropylthiomethyl)-1,4-dithiane, 2,5-bis{[2-(2,3-epithiopropylthio)ethyl]thiomethyl}-1,4-dithiane and 2,5-bis(2,3-epithiopropylthiomethyl)-2,5-dimethyl-1,4-dithiane;

aromatic 2,3-epithiopropylthio compounds such as 1,2-bis (2,3-epithiopropylthio)benzene, 1,3-bis(2,3-epithiopropylthio)benzene, 1,4-bis(2,3-epithiopropylthio)benzene, 1,2-bis(2,3-epithiopropylthiomethyl)benzene, 1,3-bis(2,3-epithiopropylthiomethyl)benzene, 1,4-bis(2,3-epithiopropylthiomethyl)benzene, bis[4-(2,3-epithiopropylthio)phenyl]methane, 2,2-bis[4-(2,3-epithiopropylthio)phenyl]propane, bis[4-(2,3-epithiopropylthio)phenyl]sulfide, bis[4-(2,3-epithiopropylthio)phenyl]sulfone and 4,4'-bis(2,3-epithiopropylthio)biphenyl; and mercapto-containing epthio compounds such as 3-mercaptopropylene sulfide and 4-mercaptobutene sulfide.

Such a (thio)epoxy compound may be subjected to addition reaction with a compound represented by general formula (1) in the presence of a tertiary amine to give a precursor of a desired thiol compound.

Examples of a compound containing an unsaturated bond which can react with a mercapto group include (meth) acrylates such as benzyl (meth)acrylate, butoxyethyl (meth) acrylate, butoxymethyl (meth)acrylate, cyclohexyl (meth) acrylate, 2-hydroxyethyl (meth)acrylate, glycidyl (meth) acrylate, thioglycidyl (meth)acrylate, phenoxyethyl (meth) acrylate, phenyl (meth)acrylate, ethyleneglycol di(meth) acrylate, diethyleneglycol di(meth)acrylate, triethyleneglycol di(meth)acrylate, tetraethyleneglycol di(meth)acrylate, polyethyleneglycol di(meth)acrylate, neopentylglycol di(meth)acrylate, bisphenol-A di(meth) acrylate, 2,2-bis(4-(meth)acryloyloxyethoxyphenyl) propane, 2,2-bis(4-(meth)acryloyloxyethoxyethoxyphenyl) propane, bisphenol-F di(meth)acrylate, bis(4-(meth) acryloyloxyethoxyphenyl)methane, 1,1-bis(4-(meth) acryloyloxyethoxyphenyl)methane, trimethylolpropane tri(meth)acrylate, glycelol di(meth)acrylate, pentaerythritol tri(meth)acrylate and pentaerythritoltetra(meth)acrylate;

thio(meth)acrylates such as (meth)acryloylthioethane, (meth)acryloylthiomethylbenzene, 1,2-bis((meth) acryloylthio)ethane, 1,3-bis((meth)acryloylthio) propane, 1,4-bis((meth)acryloylthio)butane, 1,6-bis ((meth)acryloylthio)hexane, bis(2-(meth) acryloylthioethyl)ether, bis(2-(meth)acryloylthioethyl) sulfide, bis(2-(meth)acryloylthioethylthio)methane, 1,2-bis(2-(meth)acryloylthioethylthio)-3-(meth) acryloylthiopropane, thioglycidyl thio(meth)acrylate, glycidyl thio(meth)acrylate, 1,2-bis((meth) acryloylthio)benzene, 1,3-bis((meth)acryloylthio) benzene, 1,4-bis((meth)acryloylthio)benzene, 1,2-bis ((meth)acryloylthiomethyl)benzene, 1,3-bis((meth) acryloylthiomethyl)benzene, 1,4-bis((meth) acryloylthiomethyl)benzene, 1,2-bis(2-(meth) acryloylthioethylthiomethyl)benzene, 1,3-bis(2-(meth) acryloylthioethylthiomethyl)benzene and 1,4-bis(2-(meth)acryloylthioethylthiomethyl)benzene;

allyl compounds such as allyl glycidyl ether, diallyl phthalate, diallyl tepephthalate, diallyl isophthalate, diallyl carbonate, diethyleneglycol bisallylcarbonate, diallyl sulfide and diallyl disulfide;

vinyl compounds such as styrene, chlorostyrene, methylstyrene, bromostyrene, dibromostyrene, divinylbenzene and 3,9-divinylspirobi(m-dioxane); and diisopropenylbenzene.

A compound represented by general formula (2) may be added to such a compound containing an unsaturated bond in the presence of an appropriate catalyst to form a precursor of a desired thiol compound.

Examples of an iso(thio)cyanate include aliphatic polyisocyanates such as hexamethylene diisocyanate, 2,2-dimethylpentane diisocyanate, 2,2,4-trimethylhexane diisocyanate, butene diisocyanate, 1,3-butadiene-1,4-diisocyanate, 2,4,4-trimethylhexamethylene diisocyanate, 1,6,11-undecane triisocyanate, 1,3,6-hexamethylene triisocyanate, 1,8-diisocyanato-4-isocyanatomethyloctane, bis(isocyanatoethyl) carbonate, bis(isocyanatoethyl) ether, lysine diisocyanatomethyl ester, lysine triisocyanate, xylylene diisocyanate, bis(isocyanatoethyl)benzene, bis (isocyanatopropyl)benzene, α, α, α', α'-tetramethylxylylene diisocyanate, bis(isocyanatobutyl)benzene, bis (isocyanatomethyl)naphthalene, bis (isocyanatomethylphenyl) ether, bis(isocyanatoethyl) phthalate and 2,6-di(isocyanatomethyl)furane;

alicyclic polyisocyanates such as isophorone diisocyanate, bis(isocyanatomethyl)cyclohexane, cyclohexane diisocyanate, methylcyclohexane diisocyanate, 4,4'-methylene bis (cyclohexylisocyanate), 4,4'-methylene bis(2-methylcyclohexylisocyanate), 2,5-bis (isocyanatomethyl)bicyclo[2.2.1]-heptane, 2,6-bis (isocyanatomethyl)bicyclo[2.2.1]-heptane, 3,8-bis (isocyanatomethyl)tricyclodecane, 3,9-bis (isocyanatomethyl)tricyclodecane, 4,8-bis (isocyanatomethyl)tricyclodecane and 4,9-bis (isocyanatomethyl)tricyclodecane;

aromatic polyisocyanates such as 1,2-diisocyanatobenzene, 1,3-diisocyanatobenzene, 1,4-diisocyanatobenzene, 2,4-diisocyanatotoluene, ethylphenylene diisocyanate, isopropylphenylene diisocyanate, dimethylphenylene diisocyanate, diethylphenylene diisocyanate, diisopropylphenylene diisocyanate, trimethylbenzene triisocyanate, benzene triisocyanate, biphenyl diisocyanate, toluidine diisocyanate, 4,4'-methylene bis(phenylisocyanate), 4,4'-methylene bis(2-methylphenylisocyanate), bibenzyl-4,4'-diisocyanate and bis(isocyanatophenyl) ethylene;

sulfur-containing aliphatic isocyanates such as bis (isocyanatomethyl) sulfide, bis(isocyanatoethyl) sulfide, bis(isocyanatopropyl) sulfide, bis (isocyanatohexyl) sulfide, bis(isocyanatomethyl) sulfone, bis(isocyanatomethyl) disulfide, bis (isocyanatoethyl) disulfide, bis(isocyanatopropyl) disulfide, bis(isocyanatomethylthio)methane, bis (isocyanatoethylthio)methane, bis(isocyanatoethylthio) ethane, bis(isocyanatomethylthio)ethane, 1,5-diisocyanato-2-isocyanatomethyl-3-thiapentane, 1,2,3-tris(isocyanatomethylthio)propane, 1,2,3-tris (isocyanatoethylthio)propane, 3,5-dithia-1,2,6,7-heptane tetraisocyanate, 2,6-diisocyanatomethyl-3,5-dithia-1,7-heptane diisocyanate, 2,5-diisocyanatomethylthiophene and 4-isocyanatoethylthio-2,6-dithia-1,8-octane diisocyanate;

aromatic sulfide isocyanates such as 2-isocyanatophenyl-4-isocyanatophenyl sulfide, bis(4-isocyanatophenyl) sulfide and bis(4isocyanatomethylphenyl) desulfide;

aromatic disulfide isocyanates such as bis(4-isocyanatophenyl) disulfide, bis(2-methyl-5-isocyanatophenyl) disulfide, bis (3-methyl-5- isocyanatophenyl) disulfide, bis(3-methyl-6-isocyanatophenyl) disulfide bis(4-methyl-5-isocyanatophenyl) disulfide, bis(3-methoxy-4-isocyanatophenyl) disulfide and bis(4-methoxy-3-isocyanatophenyl) disulfide;

sulfur-containing alicyclic compounds such as 2,5-diisocyanatotetrahydrothiophene, 3,4-diisocyanatomethyltetrahydrothiophene, 2,5-diisocyanato-1,4-dithiane, 2,5-diisocyanatomethyl-1,4-dithiane, 4,5-diisocyanato-1,3-dithiolane, 4,5-bis(isocyanatomethyl)-1,3-dithiolane and 4,5-diisocyanatomethyl-2-methyl-1,3-dithiolane;

aliphatic isothiocyanates such as 1,2-diisothiocyanatoethane and 1,6-diisothiocyanatohexane;

alicyclic isothiocyanates such as cyclohexane diisothiocyanate;

aromatic isothiocyanates such as 1,2-diisothiocyanatobenzene, 1,3-diisothiocyanatobenzene, 1,4-diisothiocyanatobenzene, 2,4-diisothiocyanatotoluene, 2,5-diisothiocyanato-m-xylene, 4,4'-diisothiocyanatobiphenyl, 4,4'-methylene bis(phenylisothiocyanate), 4,4'-methylene bis(2-methylphenylisothiocyanate), 4,4'-methylene bis(3-methylphenylisothiocyanate), 4,4'-isopropylidene bis(phenylisothiocyanate), 4,4'-diisothiocyanatobenzophenone, 4,4'-diisothiocyanato-3,3'-dimethylbenzophenone and bis(4-isothiocyanatophenyl) ether;

carbonylisothiocyanates such as 1,3-benzenedicarbonyl diisothiocyanate, 1,4-benzenedicarbonyl diisothiocyanate and (2,2-pyridine)-4,4-dicarbonyl diisothiocyanate;

sulfur-containing aliphatic isothiocyanates such as thiobis(3-isothiocyanatopropane), thiobis(2-isothiocyanatoethane) and dithiobis(2-isothiocyanatoethane);

sulfur-containing aromatic isothiocyanates such as 1-isothiocyanato-4-[(2-isothiocyanato)sulfonyl]benzene, thiobis(4-isothiocyanatobenzene), sulfonylbis(4-isothiocyanatobenzene) and dithiobis(4-isothiocyanatobenzene);

sulfur-containing alicyclic isothiocyanates such as 2,5-diisothiocyanatothiophene and 2,5-diisothiocyanato-1,4-dithiane; and compounds having an isocyanate and an isothiocyanate groups such as 1-isocyanato-6-isothiocyanatohexane, 1-isocyanato-4-isothiocyanatocyclohexane, 1-isocyanato-4-isothiocyanatobenzene, 4-methyl-3-isocyanato-1-isothiocyanatobenzene, 2-isocyanato-4,6-diisothiocyanato-1,3,5-triazine, 4-isocyanatophenyl-4isothiocyanatophenyl sulfide and 2-isocyanatoethyl-2-isothiocyanatoethyl disulfide.

In this invention may be used the above compounds which are halogenated (e.g., chlorinated or brominated), alkylated, alkoxylated, nitrated, modified with a polyol into a prepolymer, carbodiimide-modified, urea-modified, biuret-modified, dimerized or trimerized.

Such an iso(thio)cyanate may be subjected to an urethane-forming reaction with a compound represented by general formula (2) in the presence of a common urethane-forming catalyst such as organic tin compounds including dibutyltin dichloride, dimethyltin dichloride and dibutyltin dilaurate, and tertiary amines to give a precursor of a desired thiol compound.

Examples of a thiol compound which can react with a mercapto group include, but not limited to, aliphatic monothiol compounds such as methanethiol, ethanethiol, propanethiol, butanethiol and cyclohexanethiol;

aliphatic polythiol compounds such as methanedithiol, 1,2-ethanedithiol, 1,1-propanedithiol, 1,2-propanedithiol, 1,3-propanedithiol, 2,2-propanedithiol, 1,6-hexanedithiol, 1,2,3-propanetrithiol, 1,1-cyclohexanedithiol, 1,2-cyclohexanedithiol, 2,2-dimethylpropane-1,3-dithiol, 3,4-dimethoxybutane-1,2-dithiol, 2-methylcyclohexane-2,3-dithiol, 1,1-bis(mercaptomethyl)cyclohexane, bis(2-mercaptoethyl) thiomalate, 2,3-dimercapto-1-propanol (2-mercaptoacetate), 2,3-dimercapto-1-propanol (3-mercaptopropionate), diethyleneglycol bis(2-mercaptoacetate), diethyleneglycol bis(3-mercaptopropionate), 1,2-dimercaptopropyl methyl ether, 2,3-dimercaptopropyl methyl ether, 2,2-bis(mercaptomethyl)-1,3-propanedithiol, bis(2-mercaptoethyl) ether, ethyleneglycol bis(2-mercaptoacetate), ethyleneglycol bis(3-mercaptopropionate), trimethylolpropane bis(2-mercaptoacetate), trimethylolpropane bis(3-mercaptopropionate), pentaerythritol tetrakis(2-mercaptoacetate), pentaerythritol tetrakis(3-mercaptopropionate) and tetrakis(mercaptomethyl)methane;

aromatic monothiol compounds such as benzenethiol and toluenethiol;

aromatic polythiols such as 1,2-dimercaptobenzene, 1,3-dimercaptobenzene, 1,4-dimercaptobenzene, 1,2-bis(mercaptomethyl)benzene, 1,3-bis(mercaptomethyl)benzene, 1,4-bis(mercaptomethyl)benzene, 1,2-bis(mercaptoethyl)benzene, 1,3-bis(mercaptoethyl)benzene, 1,4-bis(mercaptoethyl)benzene, 1,2,3-trimercaptobenzene, 1,2,4-trimercaptobenzene, 1,3,5-trimercaptobenzene, 1,2,3-tris(mercaptomethyl)benzene, 1,2,4-tris(mercaptomethyl)benzene, 1,3,5-tris(mercaptomethyl)benzene, 1,2,3-tris(mercaptoethyl)benzene, 1,2,4-tris(mercaptoethyl)benzene, 1,3,5-tris(mercaptoethyl)benzene, 2,5-toluenedithiol, 3,4-toluenedithiol, 1,3-di(p-methoxyphenyl) propane-2,2-dithiol, 1,3-diphenylpropane-2,2-dithiol, phenylmethane-1,1-dithiol and 2,4-di(p-mercaptophenyl)pentane;

aromatic polythiol compounds containing a sulfur atom in addition to a mercapto group such as 1,2-bis(mercaptoethylthio)benzene, 1,3-bis(mercaptoethylthio)benzene, 1,4-bis(mercaptoethylthio)benzene, 1,2,3-tris(mercaptomethylthio)benzene, 1,2,4-tris(mercaptomethylthio)benzene, 1,3,5-tris(mercaptomethylthio)benzene, 1,2,3-tris(mercaptoethylthio)benzene, 1,2,4-tris(mercaptoethylthio)benzene and 1,3,5-tris(mercaptoethylthio)benzene as well as their nuclear alkylated derivatives;

sulfides such as bis(mercaptomethyl) sulfide, bis(mercaptoethyl) sulfide, bis(mercaptopropyl) sulfide, bis(2-mercaptoethylthio)methane, bis(3-mercaptopropylthio)methane, 1,2-bis(2-mercaptoethylthio)ethane, 1,2-bis(3-mercaptopropylthio)ethane, 1,3-bis(2-mercaptoethylthio)propane, 1,3-bis(3-mercaptopropylthio)propane, 1,2,3-tris(2-mercaptoethylthio)propane, 1,2,3-tris(3- mercaptopropylthio)propane, 1,2-bis[(2-mercaptoethyl)thio]-3-mercaptopropane, 4,8-dimercaptomethyl-1,11-dimercapto-3,6,9-trithiaundecane, 4,7-dimercaptomethyl-1,11-dimercapto-3,6,9-trithiaundecane, 5,7-dimercaptomethyl-1,11-dimercapto-3,6,9-trithiaundecane, tetrakis(2-mercaptoethylthiomethyl) methane, tetrakis(3-mercaptopropylthiomethyl) methane, bis(2,3-dimercaptopropyl) sulfide, bis(1,3-dimercaptopropyl) sulfide, 2,5-dimercapto- 1,4-dithiane, 2,5-dimercaptomethyl-1,4-dithiane, bis(mercaptoethyl) disulfide and bis(mercaptopropyl) disulfide as well as their thioglycolates and mercaptopropionates;

aliphatic polythiol compounds containing a sulfur atom in addition to a mercapto group such as hydroxymethylsulfide bis(2-mercaptoacetate), hydroxymethylsulfide bis(3-mercaptopropionate), hydroxyethylsulfide bis(2-mercaptoacetate), hydroxyethylsulfide bis(3-mercaptopropionate), hydroxypropylsulfide bis(2-mercaptoacetate), hydroxypropylsulfide bis(3-mercaptopropionate), hydroxymethyldisulfide bis(2-mercaptoacetate), hydroxymethyldisulfide bis(3-mercaptopropionate), hydroxyethyldisulfide bis(2-mercaptoacetate), hydroxyethyldisulfide bis(3-mercaptopropionate), hydroxypropyldisulfide bis(2-mercaptoacetate), hydroxypropyldisulfide bis(3-mercaptopropionate), 2-mercaptoethylether bis(2-mercaptoacetate), 2-mercaptoethylether bis(3-mercaptopropionate), 1,4-dithiane-2,5-diol bis(2-mercaptoacetate), 1,4-dithiane-2,5-diol bis(3-mercaptopropionate), bis(2-mercaptoethyl) thiodiglycolate, bis(2-mercaptoethyl) thiodipropionate, bis(2-mercaptoethyl) 4,4-thiodibutyrate, bis(2-mercaptoethyl) dithiodiglycolate, bis(2-mercaptoethyl) dithiodipropionate, bis(2-mercaptoethyl) 4,4-dithiodibutyrate, bis(2,3-dimercaptopropyl) thiodiglycolate, bis(2,3-dimercaptopropyl) thiodipropionate, bis(2,3-dimercaptopropyl) dithioglycolate and bis(2,3-dimercaptopropyl) dithiodipropionate;

heterocyclic compounds containing a sulfur atom in addition to a mercapto group such as 3,4-thiophenedithiol and 2,5-dimercapto-1,3,4-thiadiazole; and compounds containing a hydroxy group in addition to a mercapto group such as 2-mercaptoethanol, 3-mercapto-1,2-propanediol, glyceric di(mercaptoacetate), 1-hydroxy-4-mercaptocyclohexane, 2,4-dimercaptophenol, 2-mercaptohydroquine, 4-mercaptophenol, 3,4-dimercapto-2-propanol, 1,3-dimercapto-2-propanol, 2,3-dimercapto-1-propanol, 1,2-dimercapto-1,3-butanediol, pentaerythritol tris(3-mercaptopropionate), pentaerythritol mono(3-mercaptopropionate), (3-mercaptopropionate), pentaerythritol tris(thioglycolate), dipentaerythritol pentakis(3-mercaptopropionate), hydroxymethyl tris(mercaptoethylthiomethyl)methane and 1-hydroxyethylthio-3-mercaptoethylthiobenzene.

Such a thiol compound or a compound represented by general formula (2) may be converted using an oxidizing agent such as chlorine, bromine, hydrogen peroxide and sodium hypochlorite into a disulfide compound as a precursor of a desired thiol compound.

The precursor of a desired thiol compound may be converted into the thiol compound by deprotection such as hydrolysis, alcoholysis and reduction, i.e., conversion of —S—$R^2$ into —SH, depending on the type of a protective group. Specifically, deprotection may be conducted by hydrolysis or alcoholysis when —S—$R^2$ is thioester or thiourethane; and by reduction when —S—$R^2$ is disulfide. A thiol compound prepared according to this invention may be a raw material for preparation of an episulfide compound and for a resin used in an optical element such as a plastic lens. In particular, the compound may be suitably used in an eyeglass lens with a higher refractive index. In such an application, the compound is preferably a polythiol compound having at least two intramolecular mercapto groups. Particularly, a polythiol compound represented by general formula (1) may be prepared with a higher yield by applying a process of this invention.

This invention will be more specifically described.

Physical properties for a resin prepared by polymerization were evaluated by the following methods.

(1) A refractive index (nd) and Abbe number (nd): measured at 20° C. using a Pulfrich refractometer.

(2) Heat resistance: Tg was measured by TMA penetration method (load: 50 g, pinpoint: 0.5 mmf, temperature-programming rate: 10° C.).

(3) Impact resistance: according to USA FDA standards, a falling ball test was conducted by falling a 16 g steel ball on a lens with a center thickness of 1.0 mm from the height of 127 cm. The results were rated to one of three grades; A: no change, C: steel ball penetration and B: star crack.

EXAMPLE 1

Preparation of Acetylthiomethylthiol

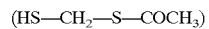

In a 3 L flask equipped with a stirring blade, a thermometer, a reflux condenser and a drain cock was placed 413 g of dibromomethane (2.38 mol) which was kept at 40° C. To the mixture was added dropwise a solution of sodium thioacetate (1291.8 g, 4.8 mol) over 6 hours and then the mixture was aged for 3 hours. To the mixture was added 1.2 L of water and then extracted organic matter with 1 L of chloroform several times.

Chloroform and components with a lower boiling point were removed by evaporation to give bis(acetylthio) methane ($CH_2$—$(S$—$COCH_3)_2$)

Then, in a 2 L flask equipped with a stirring blade, a thermometer, a reflux condenser and a drain cock were placed 370 g of bis(acetylthio)methane thus obtained (88% purity, 2 mol), 96.0 g of methanol (3 mol) and 7.6 g of p-toluenesulfonic acid (0.04 mol), and the mixture was reacted at 60° C. for 8 hours. The phases were separated by adding appropriate amounts of water and chloroform, and the chloroform phase was washed with water several times. After removing chloroform and components with a lower boiling point by evaporation, the residue was distilled at a reduced pressure (2.1 kPa, 80° C.) to give 176.0 g of acetylthiomethylthiol (1.4 mol).

In its IR spectrum obtained using FTIR-8300 (SIMADZU), there were observed characteristic absorptions of thiol at 2538.1 $cm^{-1}$ and of carbonyl at 1689.5 $cm^{-1}$.

Mass Spectrum: m/z=122 ($M^+$);

Elemental analysis:

Observed: C: 29.5%; H: 4.8%; S: 52.3%

Calculated: C: 29.5%; H: 5.0%; S: 52.5%

Preparation of 1,1,3,3-tetrakis-(mercaptomethylthio) propane

In a 2 L flask equipped with a stirring blade, a thermometer, a distillation column, a nitrogen-inlet capillary and a drain cock were placed 164.2 g of 1,1,3,3-tetramethoxypropane (1 mol), 488.8 g of acetylthiomethylthiol (4 mol) and 7.6 g of p-toluenesulfonic acid (0.04 mol), and while keeping a vacuum of 1 kPa or less, the mixture was heated at 55 to 60° C. with stirring. Heating was continued for about 5 hours until methanol distillation ceased. After cooling, breaking vacuum and then replacing the distillation column with a reflux condenser, to the mixture were added 400 mL of methanol and 400 mL of chloroform. The mixture was heated at 60° C. for alcoholysis to form desired 1,1,3,3-tetrakis(mercaptomethylthio)propane represented by the following formula (hereinafter, referred to as Compound (A)).

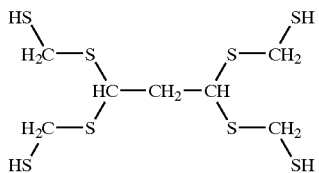

After adding appropriate amounts of water and chloroform, the phases were separated and the chloroform layer was washed with water several times. After removing chloroform and components with a lower boiling point by evaporation, the residue was filtrated through a 3 mm Teflon$^a$filter to give 340.0 g of Compound (A).

The satisfactorily high yield was obtained, i.e., 95.3% from 1,1,3,3-tetramethoxypropane.

In its IR spectrum obtained using FTIR-8300 (SIMADZU), there was observed a characteristic absorption of mercapto at 2538.1 cm$^{-1}$.

Mass Spectrum: m/z=356 (M$^+$);
Elemental analysis:
Observed: C: 23.5%; H: 4.6%; S: 71.9%
Calculated: C: 23.6%; H: 4.5%; S: 71.9%

EXAMPLE 2

Preparation of 1,1,2,2-tetrakis-(mercaptomethylthio)ethane

In a 2 L flask equipped with a stirring blade, a thermometer, a distillation column, a nitrogen-inlet capillary and a drain cock were placed 150.2 g of 1,1,2,2-tetramethoxyethane (1 mol), 488.8 g of acetylthiomethylthiol (4 mol) and 7.6 g of p-toluenesulfonic acid (0.04 mol), and while keeping a vacuum of 1 kPa or less, the mixture was heated at 55 to 60° C. with stirring. Heating was continued for about 5 hours until methanol distillation ceased. After cooling and breaking vacuum, to the mixture were added 400 mL of methanol and 400 mL of chloroform. The mixture was heated at 60° C. for alcoholysis to form desired 1,1,2,2-tetrakis(mercaptomethylthio)ethane represented by the following formula (hereinafter, referred to as Compound (B)).

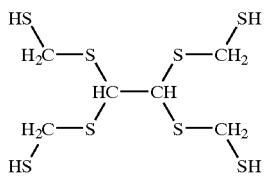

After adding appropriate amounts of water and chloroform, the phases were separated and the chloroform layer was washed with water several times. After removing chloroform and components with a lower boiling point by evaporation, the residue was filtrated through a 3 mm Teflon$^a$filter to give 321.1 g of Compound (B)).

The satisfactorily high yield was obtained, i.e., 93.7% from 1,1,2,2-tetramethoxyethane.

In its IR spectrum obtained using FTIR-8300 (SIMADZU), there was observed a characteristic absorption of mercapto at 2522.7 cm$^{-1}$.

Mass Spectrum: m/z=342 (M$^+$);
Elemental analysis:
Observed: C: 20.8%; H: 4.2%; S: 75.9%
Calculated: C: 21.0%; H: 4.1%; S: 74.9%

EXAMPLE 3

To 44.7 g of bis(isocyanatomethyl) sulfide (hereinafter, referred to as Compound (E)) were added 30 mg of dibutyltin dichloride (hereinafter, referred to as Compound (F)) as a catalyst, 150 mg of "Zelec UN" (Trade Name, Stepan Co. Ltd., acidic alkyl phosphate; hereinafter, referred to as Compound (G)) as an internal mold release agent and 50 mg of "VIOSORBO 583" (Trade Name, Kyodo Yakuhin Co. Ltd.; hereinafter, referred to as Compound (H)) as a UV absorber to give a mixed solution. To the solution was added 55.3 g of Compound (A), and the mixture was sufficiently mixed to give a monomer mixture. After degassing at 0.6 kPa for 1 hour, a part of the monomer mixture was injected into a lens mold, gradually heated from 40° C. to 130° C. and cured for 20 hours. After cooling, the glass mold was removed to give a lens. The lens was colorless and transparent, and turbidity was not observed when passing light through the lens using a slide projector in a dark room. It exhibited good optical properties (refractive index (nd): 1.705 and Abbe number (nd): 32); and good heat resistance (Tg point: 107.8° C.). Its impact resistance was rated to "A".

EXAMPLE 4

To 51.4 g of m-xylyelnediisocyanate (hereinafter, referred to as Compound (I)) were added 30 mg of Compound (F) as a catalyst, 150 mg of Compound (G) as an internal mold release agent and 50 mg of Compound (H) as a UV absorber to give a mixed solution. To the solution was added 48.6 g of Compound (A), and the mixture was sufficiently mixed to give a monomer mixture. After degassing at 0.6 kPa for 1 hour, a part of the monomer mixture was injected into a lens mold, gradually heated from 40° C. to 130° C. and cured for 20 hours. After cooling, the glass mold was removed to give a lens. The lens was colorless and transparent, and turbidity was not observed when passing light through the lens using a slide projector in a dark room. It exhibited good optical properties (refractive index (nd): 1.683 and Abbe number (nd): 30); and good heat resistance (Tg point: 113.2° C.). Its impact resistance was rated to "A".

EXAMPLE 5

To 45.7 g of Compound (E) were added 30 mg of Compound (F) as a catalyst, 150 mg of Compound (G) as an internal mold release agent and 50 mg of Compound (H) as a UV absorber to give a mixed solution. To the solution was added 54.3 g of Compound (B), and the mixture was sufficiently mixed to give a monomer mixture. After degassing at 0.6 kPa for 1 hour, a part of the monomer mixture was injected into a lens mold, gradually heated from 40° C. to 130° C. and cured for 20 hours. After cooling, the glass mold was removed to give a lens. The lens was colorless and transparent, and turbidity was not observed when passing light through the lens using a slide projector in a dark room. It exhibited good optical properties (refractive index (nd): 1.721 and Abbe number (nd): 32); and good heat resistance (Tg point: 108.5° C.). Its impact resistance was rated to "A".

EXAMPLE 6

To 52.4 g of Compound (I) were added 30 mg of Compound (F) as a catalyst, 150 mg of Compound (G) as an internal mold release agent and 50 mg of Compound (H) as a UV absorber to give a mixed solution. To the solution was added 47.6 g of Compound (B), and the mixture was sufficiently mixed to give a monomer mixture. After degassing at 0.6 kPa for 1 hour, a part of the monomer mixture was injected into a lens mold, gradually heated from 40° C. to 130° C. and cured for 20 hours. After cooling, the glass mold was removed to give a lens. The lens was colorless and transparent, and turbidity was not observed when passing light through the lens using a slide projector in a dark room. It exhibited good optical properties (refractive index (nd): 1.699 and Abbe number (nd): 30); and good heat resistance (Tg point: 115.2° C.). Its impact resistance was rated to "A".

COMPARATIVE EXAMPLE 1

To 44.0 g of Compound (E) were added 15 mg of Compound (F) as a catalyst, 150 mg of Compound (G) as an internal mold release agent and 50 mg of Compound (H) as a UV absorber to give a mixed solution. To the solution was added 56.0 g of a mixture of 4,8-dimercaptomethyl-1,11-dimercapto-3,6,9-trithiaundecane, 4,7-dimercaptomethyl-1,11dimercapto-3,6,9-trithiaundecane and 5,7-dimercaptomethyl-1,11-3,6,9-trithiaundecane (hereinafter, referred to as Mixture (L)), and the mixture was sufficiently mixed to give a monomer mixture. After degassing at 0.6 kPa for 1 hour, a part of the monomer mixture was injected into a lens mold, gradually heated from 40° C. to 130° C. and cured for 20 hours. After cooling, the glass mold was removed to give a lens. The lens was colorless and transparent, and turbidity was not observed when passing light through the lens using a slide projector in a dark room. It exhibited a refractive index (nd) of 1.680, an Abbe number (nd) of 34, a heat resistance (Tg point) of 92.5° C. and impact resistance rated to "A".

The lens had comparable impact resistance, but inferior optical properties and heat resistance to that in Example 5.

COMPARATIVE EXAMPLE 2

A mixture of 22.9 g of {1,2-bis((2-mercaptoethyl)thio)-3-mercaptopropane} (hereinafter, referred to as Compound (M)) (0.088 mol), 24.9 g of Compound (I) (0.132 mol), 9.6 mg of Compound (F) (200 ppm) as a curing catalyst, 24.0 mg of Compound (J) (500 ppm) as a UV absorber and 72.0 mg of Compound (K) (1500 ppm) as an internal mold release agent was homogeneously mixed and dissolved with degassing under a reduced pressure, and then injected into a mold consisting of a glass mold and a gasket.

The mixture was reacted by gradually heating the mold from 40° C. to 130° C. and cured by heating for 20 hours. After polymerization, the mold was gradually cooled, and a polymer was removed from the mold.

The urethane lens thus obtained was transparent, and exhibited a refractive index of 1.665, an Abbe number of 32, a heat resistance of 85° C. and impact resistance rated to "A". The lens exhibited a lower refractive index than those in Examples 5 to 12.

COMPARATIVE EXAMPLE 3

To 100.0 g of bis(2,3-epithiopropyl) sulfide was added 0.2 g of N,N-dimethylcyclohexylamine and the mixture was well mixed. After degassing at 0.6 kPa for 0.5 hours, the mixture was injected into a lens mold. The mold was gradually heated from 30° C. to 120° C., and cured for 24 hours. After cooling, the glass mold was removed to give a lens. The lens thus obtained was colorless and transparent, and turbidity was not observed when passing light through the lens using a slide projector in a dark room. Its optical properties were a refractive index (nd) of 1.701 and an Abbe number (nd) of 36. It exhibited a heat resistance (Tg) of 82.0° C. and impact resistance rated to "C".

The lens exhibited inferior impact resistance to those in Examples.

The results in Examples 3 to 6 and Comparative Examples 1 to 3 are shown in Table 1.

TABLE 1

|  | Polythiol | Polyisocyanate | Refractive Index | Abbe Number | Heat Resistance (° C.) | Impact Resistance |
|---|---|---|---|---|---|---|
| Exam. 3 | (A) | (E) | 1.705 | 32 | 107.8 | A |
| Exam. 4 | (A) | (I) | 1.683 | 30 | 113.2 | A |
| Exam. 5 | (B) | (E) | 1.721 | 32 | 108.5 | A |
| Exam. 6 | (B) | (I) | 1.699 | 30 | 115.2 | A |
| Comp. Exam. 1 | (L) | (E) | 1.680 | 34 | 92.5 | A |
| Comp. Exam. 2 | (M) | (I) | 1.665 | 32 | 85.0 | A |
| Comp. Exam. 3 | — | — | 1.701 | 36 | 82.0 | C |

What is claimed is:

1. A polythiol compound represented by the general formula (1):

$$R-(SCH_2SH)_n \quad (1)$$

where R is an organic residue except for an aromatic group and n is an integer of at least 1, having at least two intramolecular mercapto groups and at least one dithioacetal skeleton represented by the following formula:

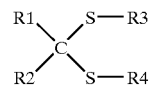

where R1 and R2 are each independently a hydrogen atom or an organic residue except for an aromatic group, which may contain a mercapto group; R3 and R4 are each independently an organic residue except for an aromatic group, which may contain a mercapto group; R1 and R2 are not simultaneously a hydrogen atom; and R1 and R2, R1 and R3 or R4, R2 and R3 or R4, and R3 and R4 may be bonded to form a ring.

2. The polythiol compound as claimed in claim 1 wherein the organic residue is selected from the group consisting of aliphatic, alicyclic and heterocyclic radicals as well as aliphatic, alicyclic and heterocyclic radicals containing a sulfur atom in their chain.

3. The polythiol compound as claimed in claim 1 wherein the compound represented by general formula (1) is selected from the group consisting of 3,3-dimercaptomethyl-1,5-dimercapto-2,4-dithiapentane, 3-mercapto-methyl-1,5-dimercapto-2,4-dithiapentane, 3-mercapto-methyl-1,5dimercapto-2,4-dithiapentane, 3-mercaptomethylthio-1,5dimercapto-2-thiapentane, 1,1,2,2-tetrakis(mercaptomethylthio)ethane, 1,1,3,3-tetrakis(mercaptomethylthio)propane, 4,5-bis(mercapto-methylthio)-1,3-dithiolan, 4,6-bis(mercaptomethylthio)-1,3-dithian,2-bis(mercaptomethylthio) methyl-1,3-dithiethane, 2-(2,2-bis(mercapto-methylthio)methyl1,3-dithiethane.

4. The polythiol compound as claimed in claim 1 wherein the compound represented by general formula (1) is 1,1,3,3-tetrakis(mercaptomethylthio)propane.

5. The polythiol compound as claimed in claim 1 wherein the compound represented by general formula (1) is 1,1,2,2-tetrakis (mercaptomethylthio)ethane.

6. The polythiol compound as claimed in claim 1 wherein the compound represented by general formula (1) is 3-mercaptomethyl-1,5-dimercapto-2, 4-dithiapentane.

* * * * *